(12) United States Patent
Lonero (10) Patent No.: US 8,431,766 B1
(45) Date of Patent: Apr. 30, 2013

(54) DIAPER WITH WETNESS DETECTING SYSTEM

(76) Inventor: Patrick H. Lonero, Phoenix, AZ (US)

( * ) Notice: Subject to any disclaimer, the term of this patent is extended or adjusted under 35 U.S.C. 154(b) by 261 days.

(21) Appl. No.: 12/773,286

(22) Filed: May 4, 2010

Related U.S. Application Data (60) Provisional application No. 61/215,458, filed on May 6, 2009.

(51) Int. Cl.
*A61F 13/15* (2006.01)

(52) U.S. Cl.
USPC .......................................................... 604/361

(58) Field of Classification Search .................... 604/361
See application file for complete search history.

(56) References Cited

U.S. PATENT DOCUMENTS

| | | | | |
|---|---|---|---|---|
| 4,768,023 A | * | 8/1988 | Xie | ............................ 340/573.5 |
| 5,036,859 A | * | 8/1991 | Brown | ........................... 600/547 |
| 5,469,146 A | | 11/1995 | Gurler | |
| 5,568,128 A | | 10/1996 | Nair | |
| 5,838,240 A | * | 11/1998 | Johnson | ......................... 340/604 |
| 6,163,262 A | | 12/2000 | Wu | |
| 6,573,837 B2 | * | 6/2003 | Bluteau | .......................... 340/604 |
| 6,580,013 B1 | * | 6/2003 | Belloso | ........................... 604/361 |
| 7,352,286 B2 | | 4/2008 | Chan et al. | |
| 7,667,608 B2 | | 2/2010 | Ales et al. | |
| 7,956,754 B2 | * | 6/2011 | Long | ............................ 340/573.5 |
| 2004/0147888 A1 | * | 7/2004 | Huang et al. | .................. 604/361 |
| 2010/0137819 A1 | * | 6/2010 | Wada et al. | .................... 604/319 |

* cited by examiner

*Primary Examiner* — Lynne Anderson
*Assistant Examiner* — Bradley Philips
(74) *Attorney, Agent, or Firm* — Parsons & Goltry; Michael W. Goltry; Robert A. Parsons (57) ABSTRACT

A diaper apparatus includes a diaper having absorbent material formed between inner surfaces of opposed inner and outer layers each having an outer surface. Two conductors are applied to the diaper, and a mounting plate is affixed to the outer surface of the outer layer of the diaper with fasteners formed with electrical connectors electrically connected to the two conductors, respectively. An alarm unit having two complementing electrical connectors, and an alarm electrically connected to the two complementing electrical connectors. The electrical connectors detachably secure the complementing electrical connectors detachably securing the alarm unit to the mounting plate and electrically connecting the electrical connectors to the complementing electrical connectors. The alarm of the alarm issues an alarm stimulus in response to wetness applied to the diaper electrically connecting the two conductors applied to the diaper.

11 Claims, 5 Drawing Sheets

DIAPER WITH WETNESS DETECTING SYSTEM

CROSS-REFERENCE TO RELATED APPLICATION

This application claims the benefit of U.S. Provisional Patent Application Ser. No. 61/215,458, filed May 6, 2009.

FIELD OF THE INVENTION

The present invention relates to diapers and, more particularly, diapers formed with wetness detecting systems.

BACKGROUND OF THE INVENTION

A diaper is a garment worn normally individuals who are not able to control their bladder or bowel movements. When a diaper becomes full and can no longer hold additional waste material, it must be changed, such as by a caregiver. Failure to change a diaper on a regular basis can lead to diaper rash.

To ensure regular diaper changes, skilled artisans have developed a variety of systems designed to detect the presence of waste in a diaper, and to issue a resulting alarm, such as an audible or visual alarm, to alert a caregiver that the diaper needs to be changed. However, existing waste detection systems and diapers formed with such systems are expensive, difficult to construct, and, most importantly, impractical. Given these and other deficiencies in the art, the need for a diaper with an improved wetness detecting system is needed.

SUMMARY OF THE INVENTION

According to the principle of the invention, a diaper apparatus consists of a diaper including opposed inner and outer layers, each having an inner surface and an opposed outer surface, and absorbent material formed between the inner surfaces of the opposed inner and outer layers. Two conductors are applied to the diaper, and are positioned to interact with wetness applied to the diaper, such as urine. A substantially rigid mounting plate, which is formed with two electrical connectors, is affixed to the diaper. The mounting plate has an inner face applied against the outer surface of the outer layer of the diaper and an opposed outer face. The two electrical connectors are electrically connected to the two conductors, respectively, and project outward with respect to the outer face of the mounting plate. An alarm unit has two complementing electrical connectors, and an alarm electrically connected to the two complementing electrical connectors. The two electrical connectors of the mounting plate are for detachably securing the two complementing electrical conductors, respectively, of the alarm unit for detachably securing the alarm unit to the mounting plate in juxtaposition to the outer face of the mounting plate and electrically connecting the two electrical connectors of the mounting plate to the two complementing electrical connectors of the alarm unit. According to this embodiment, the electrical connectors of the mounting plate are detachably secured to the complementing electrical connectors, respectively, of the alarm unit detachably securing the alarm unit to the mounting plate in juxtaposition to the outer face of the mounting plate, and electrically connecting the two electrical connectors of the mounting plate to the two complementing electrical connectors of the alarm unit, and the alarm of the alarm unit issues an alarm stimulus, such as an audible stimulus a visual stimulus or both, in response to wetness applied to the diaper electrically connecting the two conductors applied to the diaper. Each electrical connector of the mounting plate is one of a male electrical connector and a female electrical connector, and each complementing electrical connector of the alarm unit is the other of the male electrical connector and the female electrical connector. In a further and more specific aspect, the two electrical connectors of the mounting plate snap engage and secure the two complementing electrical connectors of the alarm unit detachably securing the alarm unit to the mounting plate in juxtaposition to the outer face of the mounting plate.

According to the principle of the invention, a diaper apparatus consists of a diaper including opposed inner and outer layers, each having an inner surface and an opposed outer surface, and absorbent material formed between the inner surfaces of the opposed inner and outer layers. Two conductors are applied to the diaper, and are positioned to be electrically connected by wetness applied to the diaper, such as urine. A substantially rigid mounting plate is affixed to the diaper with two fasteners each formed with an electrical connector. The mounting plate has an inner face applied against the outer surface of the outer layer of the diaper and an opposed outer face. The two electrical connectors of the two fasteners are electrically connected to the two conductors, are juxtaposed with respect to the outer face of the mounting plate, and project outward with respect to the outer face of the mounting plate. An alarm unit has two complementing electrical connectors, and an alarm electrically connected to the two complementing electrical connectors. The two electrical connectors of the fasteners are for detachably securing the two complementing electrical conductors, respectively, of the alarm unit for carrying out two functions, namely, for detachably securing the alarm unit to the mounting plate in juxtaposition to the outer face of the mounting plate, and electrically connecting the two electrical connectors of the fasteners to the two complementing electrical connectors of the alarm unit. Each electrical connector is one of a male electrical connector and a female electrical connector, and each complementing electrical connector is the other of the male electrical connector and the female electrical connector. In a further and more specific aspect, the electrical connectors are snap electrical connectors, and the complementing electrical connectors are complementing snap electrical connectors to snappingly engage and secure the snap electrical connectors, respectively. The fasteners are preferably electrically conducting rivets.

According to the principle of the invention, a diaper apparatus consists of a diaper including opposed inner and outer layers, each having an inner surface and an opposed outer surface, and absorbent material formed between the inner surfaces of the opposed inner and outer layers. Two conductors are applied to the diaper, and are positioned to be electrically connected by wetness applied to the diaper, such as urine. A substantially rigid mounting plate is affixed to the diaper with two fasteners. The fasteners are each formed with an electrical connector. The mounting plate has an inner face applied against the outer surface of the outer layer of the diaper and an opposed outer face. The two electrical connectors are juxtaposed with respect to the outer face of the mounting plate and project outward with respect to the outer face of the mounting plate. The two electrical connectors of the two fasteners are electrically connected to the two conductors, respectively. An alarm unit has two complementing electrical connectors, and an alarm electrically connected to the two complementing electrical connectors. The two electrical connectors of the fasteners are detachably securing the two complementing electrical conductors, respectively, of the alarm unit thereby carrying out two functions, namely, detachably securing the alarm unit to the mounting plate in juxtaposition to the outer face of the mounting plate, and electrically connecting the two electrical connectors of the fasteners to the two complementing electrical connectors of the alarm unit. The alarm of the alarm unit issues an alarm stimulus, such as an audible stimulus a visual stimulus or both, in response to wetness applied to the diaper electrically connecting the two conductors applied to the diaper. Each electrical connector is one of a male electrical connector and a female electrical connector, and each complementing electrical connector is the other of the male electrical connector and the female electrical connector. In a further and more specific aspect, the electrical connectors are snap electrical connectors, and the complementing electrical connectors are complementing snap electrical connectors snappingly engaging and securing the snap electrical connectors, respectively. The fasteners are preferably electrically conducting rivets.

Consistent with the foregoing summary of preferred embodiments, and the ensuing detailed description, which are to be taken together, the invention also contemplates associated apparatus and method embodiments.

BRIEF DESCRIPTION OF THE DRAWINGS

Referring to the drawings.

DETAILED DESCRIPTION

Figure 1:
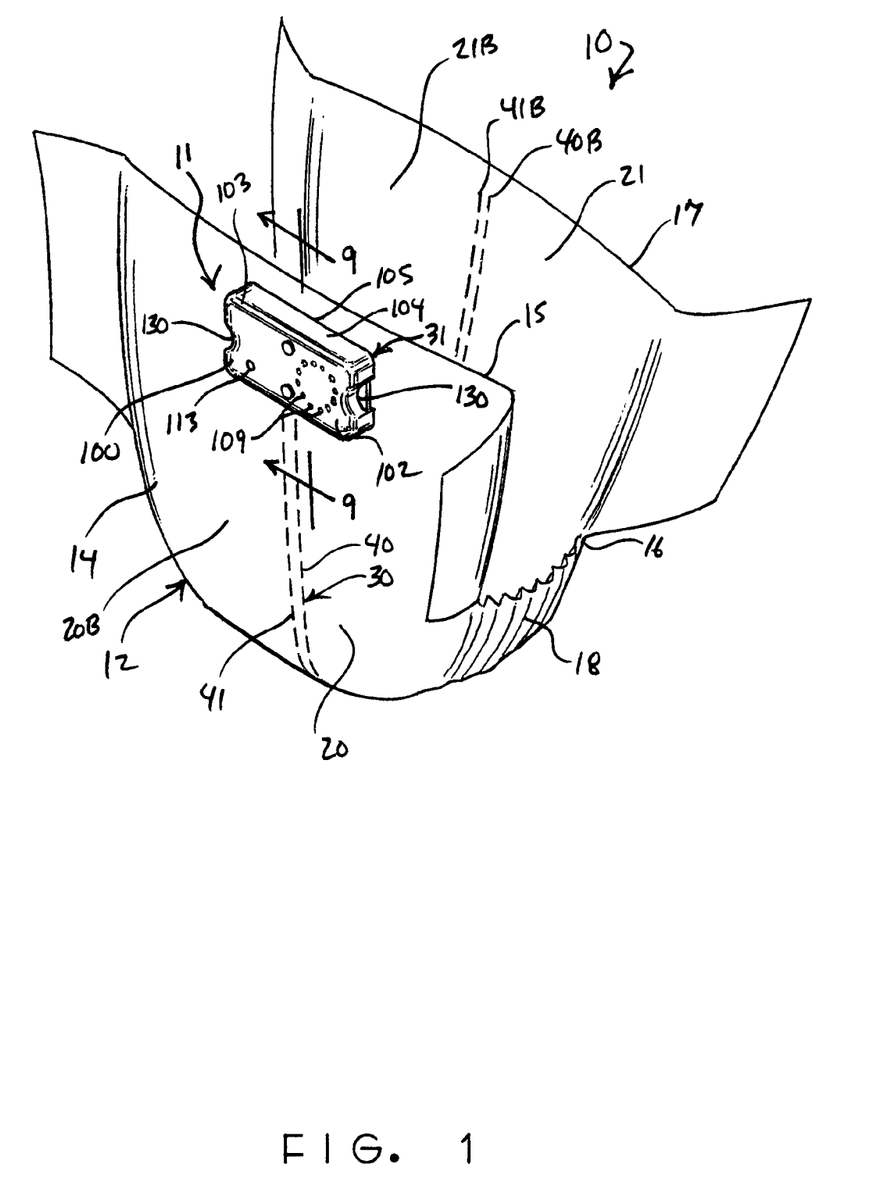
FIG. 1 is a diaper apparatus constructed and arranged in accordance with the principle of the invention, the diaper apparatus including a diaper formed with a wetness detecting system including conductors, indicated by opposed, parallel dotted lines, positioned to be exposed to wetness applied to the diaper, and an attached alarm unit.

Turning now to the drawings, in which like reference characters indicate corresponding elements throughout the several views, attention is first directed to FIG. 1 in which there is seen a diaper apparatus 10 constructed and arranged in accordance with the principle of the invention including a wetness detecting system 11 formed with a diaper 12 including a front panel 14 that terminates at a top edge 15, an opposed rear panel 16 that terminates with a top edge 17, and opposed ribbed panels 18 (only one shown) connecting front and rear panels 14 and 16. Diaper 12 is a conventionally-structured, modern disposable diaper having a layered construction, which allows the transfer and distribution of urine to an absorbent material or core formed in diaper 12. In reference to FIG. 8, which is a section view take along line 8-8 of FIG. 1, the basic layers are an outer shell or layer 20 having opposed inner and outer surfaces 20A and 20B, an opposed inner layer 21 having opposed inner and outer surfaces 21A and 21B, and an absorbent core or material 22 formed between inner surfaces 20A and 21A of outer and inner layers 20 and 21, respectively. Outer shell or layer 20 is formed of a breathable polyethylene film or a nonwoven and film composite that prevents wetness and soil transfer, inner shell or layer 21 nearest the skin of a user wearing diaper 12 is made of nonwoven material with a distribution layer directly beneath that transfers wetness to absorbent core or material 22, and absorbent core or material 22 is a mixture of air-laid paper and superabsorbent polymers for wetness. This layered construction is shown in front panel 14 in FIG. 8, and is also present in rear panel 16.

As indicated above, diaper 12 is exemplary of a conventional and well-known modern disposable diaper, and is set forth for the purposes of orientation and reference, further details of which are well known and will readily occur to the skilled artisan and are not discussed in further detail. System 11 is incorporated with diaper 12 thus forming diaper apparatus 10 in accordance with the principle of the invention. Diaper 12 is illustrative of a type of diaper useful with system 11, and system 11 can be incorporated with other diaper forms to form the diaper apparatus in accordance with the invention.

Figure 2:
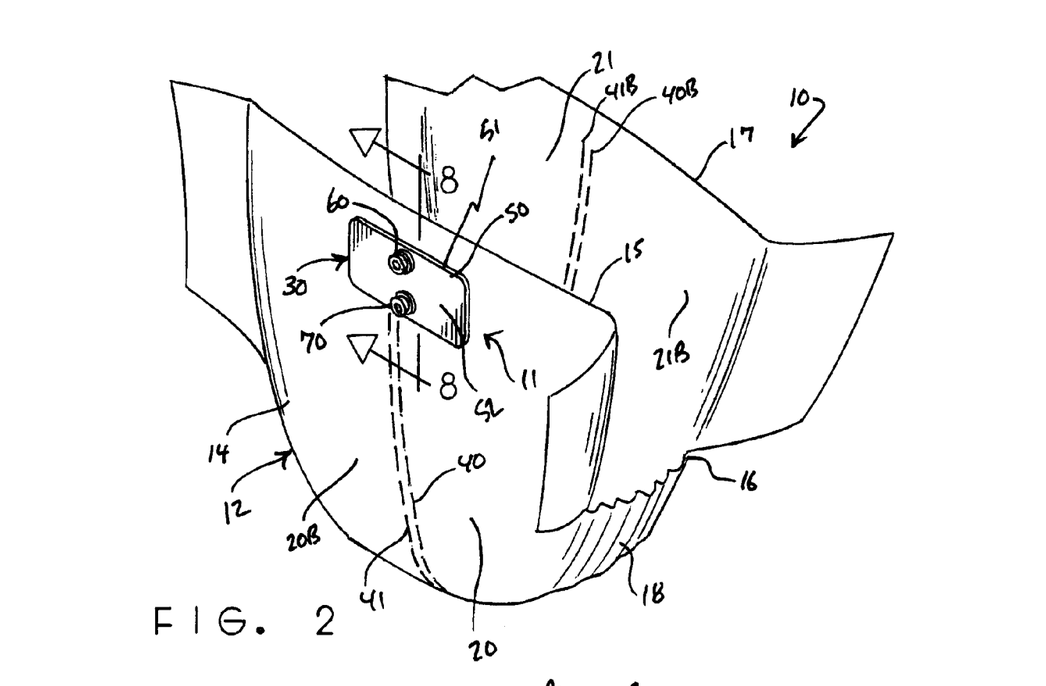
FIG. 2 is a view similar to that of FIG. 1 illustrating the diaper apparatus as it would appear with the alarm unit detached depicting a conductor assembly of the wetness detecting system including a mounting plate formed with electrical connectors electrically connected to the conductors depicted by opposed, parallel dotted lines.
Figure 3:
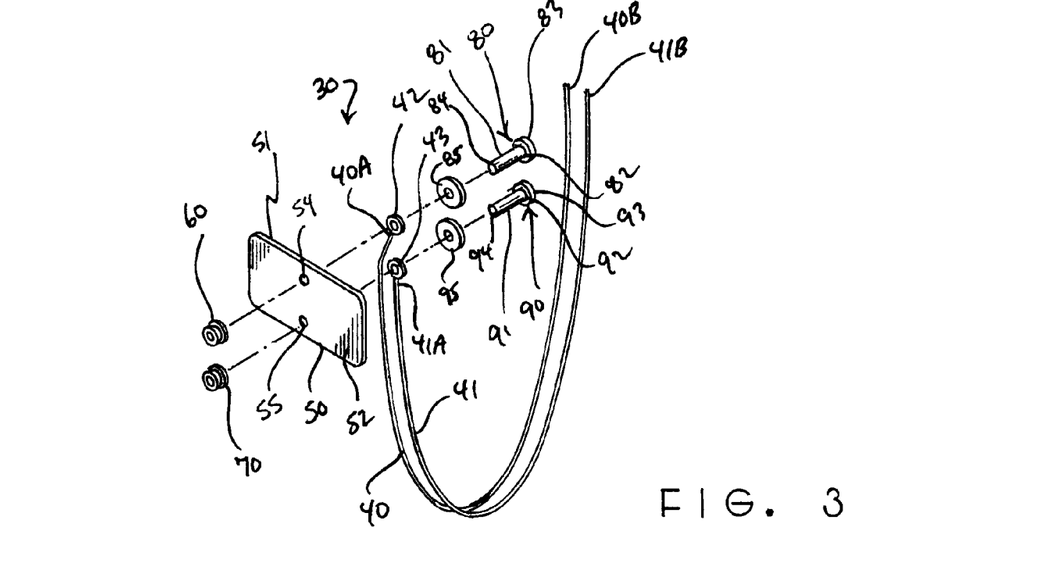
FIG. 3 is an exploded view of a conductor assembly of FIG. 2.

System consists of a conductor assembly formed with diaper 12, which is generally indicated by the reference numeral 30 in FIGS. 1-3, and an alarm unit generally denoted by the reference numeral 31 in FIG. 1. Conductor assembly 30 is applied to diaper 12, and alarm unit 31 is configured to be removably and operatively coupled to conductor assembly 30, in which the alarm unit 31 operates to issue an alarm stimulus in response to wetness applied to the conductor assembly 30 formed with diaper 12 closing a circuit formed between conductor assembly 30 and alarm unit 31.

Conductor assembly 30 consists of two conductors 40 and 41, a mounting plate 50 secured to diaper 12 with two fasteners denoted generally at 80 and 90, and two electrical connectors 60 and 70. Electrical connectors 6 and 70 are formed with fasteners 80 and 90, respectively, and form part of fasteners 80 and 90, respectively. Conductors 40 and 41 are formed of conductive foil or wire, are elongate and substantially coextensive, and have inner ends 40A and 41A and opposed outer ends 40B and 41B, respectively. Conductors 40 and 41 are denoted in dotted outline in FIGS. 1 and 2 indicating the relative positioning and orientation of conductors 40 and 41 with respect to diaper 12. Conductors 40 and 41 are applied to or otherwise extend through diaper 12 between inner surfaces 20A and 21A of outer and inner layers 20 and 21 and are so positioned to interact with wetness applied to diaper 12. Preferably, conductors 40 and 41 are positioned in and extend through absorbent core or material 22, as substantially shown in FIG. 8, formed between inner surfaces 20A and 21A of outer and inner layers 20 and 21 of front and rear panels 14 and 16. This positioning of conductors 40 and 41 in diaper 12 allows conductors 40 and 41 to interact with wetness applied to diaper 12.

As seen in FIGS. 1 and 2, conductors 40 and 41 are located at and extend through front and rear panels 14 and 16, and are located at a generally intermediate position in front and rear panels 14 and 16 between ribbed panels 18 (only one shown). Outer ends 40B and 41B of conductors 40 and 41 are directed toward edge 17 of rear panel 16 at a generally intermediate position of rear panel 16, inner ends 40A and 41A of conductors 40 and 41 are directed toward edge 15 of front panel 14 and are positioned at a generally intermediate position of front panel 14, and conductors 40 and 41 extend through diaper 12 from outer ends 40B and 41B proximate to edge 17 through rear panel 16 and then through front panel 14 terminating with inner ends 40A and 41A located proximate to edge 15 of front panel 14 at a generally intermediate position of front panel 14.

Mounting plate 50 is applied to outer surface 20B of outer layer 20 of front panel 14 of diaper 12 at a generally intermediate position of front panel 14 beneath edge 15 and opposing inner ends 40A and 41A of conductors 40 and 41 as seen in FIG. 2. Mounting plate 50 is fashioned of plastic, ceramic, or other substantially rigid material or combination of materials, and is preferably nonconductive. Mounting plate 50 is broad and flat, and has an inner face 51 denoted in FIGS. 2, 3, 8, and 9, and an opposed outer face 52, and is generally rectangular in shape in the present embodiment. Referencing FIGS. 3, 8, and 9, mounting plate 50 is secured to diaper with fasteners 80 and 90. Inner ends 40A and 41A are electrically connected to fasteners 80 and 90, electrical connectors 60 and 70 are secured to and form part of fasteners 80 and 90, respectively, and are electrically connected to fasteners 80 and 90, respectively, which electrically connects electrical connectors 60 and 70 to conductors 40 and 41. Electrical connectors 60 and 70 form part of fasteners 80 and 90, respectively, and are thus associated with mounting plate 50.

Figure 8:
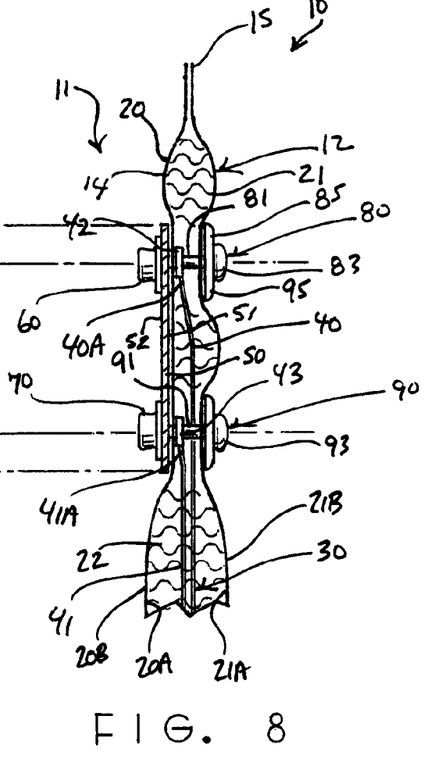
FIG. 8 is a section view taken along line 8-8 of FIG. 2.
Figure 9:
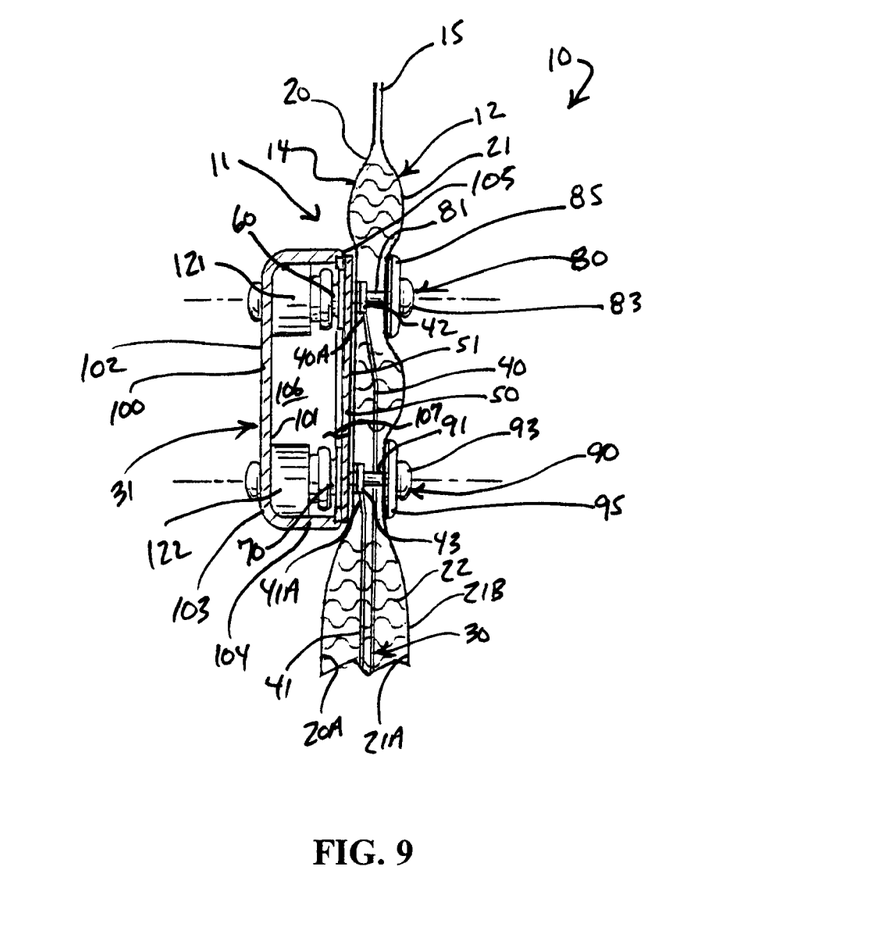
FIG. 9 is a section view taken along line 9-9 of FIG. 1.

Inner face 51 of mounting plate 50 is applied to outer surface 20B of outer layer 20 of front panel 14 of diaper 12, and is mounted to front panel 14 of diaper 12 proximate to edge 15 at a generally intermediate position of front panel 14 as shown in FIG. 2 opposite to inner ends 40A and 41A of conductors 40 and 41 as shown in FIGS. 8 and 9. Outer face 52 of mounting plate 50 faces outwardly with respect to outer surface 20A of outer layer 20 of front wall 14 of diaper 12, and electrical connectors 60 and 70 secured to fasteners 80 and 90, respectively, are positioned in juxtaposition with respect to outer face 52 of mounting plate 50, and project outward with respect to outer face 52 of mounting plate 50.

Looking specifically to FIG. 3, inner end 40A of conductor 40 is formed with a small, circular washer 42, and inner end 41A of conductor 41 is likewise formed with a small, circular washer 43. Fastener 80 is a rivet consisting of a smooth, cylindrical shaft 81 having an inner end 82 formed with an enlarged head 83, and an opposed outer end 84. Fastener 90 is also a rivet consisting of a smooth, cylindrical shaft 91 having an inner end 92 formed with an enlarged head 93, and an opposed outer end 94.

Referencing FIGS. 3 and 8 in relevant part, washer 85 encircles shaft 81 and is positioned against the inner side of head 83 at inner end 82 (not referenced in FIG. 8) of shaft 81 of fastener 80. Shaft 81 extends through diaper 12 from inner layer 21, through absorbent material 22, and through outer layer 20. Washer 85 encircling shaft 81 of fastener 80 is captured by, and is applied between, outer surface 21B of inner layer 21 of diaper 12 and head 83 received in juxtaposition to outer surface 21B of inner layer 21 of diaper 12. Washer 42 positioned between inner surfaces 20A and 21A of outer and inner layers 20 and 21, respectively, encircles and contacts shaft 81 between inner and outer ends 82 and 84 of fastener 80. Outer end 84 of shaft 81 is received into and through an opening 54 formed through mounting plate 50, and is, in turn, received by, and secured to, electrical connector 60, which is juxtaposed along outer face 52 of mounting plate 50. Electrical connector 60 is preferably press fit onto outer end 84 of shaft 81. Mounting plate 50 and front panel 14 of diaper 12 are captured by and between washer 85 captured by and between head 83 of fastener 80 and outer surface 21B of inner layer 21 of front panel 14 of diaper 12, and electrical connector 60 applied against outer face 52 of mounting plate 50.

Washer 95 encircles shaft 91 and is positioned against the inner side of head 93 at inner end 92 (not referenced in FIG. 9) of shaft 91 of fastener 90. Shaft 91 extends through diaper 12 from inner layer 21, through absorbent material 22, and through outer layer 20. Washer 95 encircling shaft 91 of fastener 90 is captured by, and is applied between, outer surface 21B of inner layer 21 of diaper 12 and head 93 received in juxtaposition to outer surface 21B of inner layer 21 of diaper 12. Washer 43 positioned between inner surfaces 20A and 21A of outer and inner layers 20 and 21, respectively, encircles and contacts shaft 91 between inner and outer ends 92 and 94 of fastener 90. Outer end 94 of shaft 91 is received into and through an opening 54 formed through mounting plate 50, and is, in turn, received by, and secured to, electrical connector 70, which is juxtaposed along outer face 52 of mounting plate 50. Electrical connector 70 is preferably press fit onto outer end 94 of shaft 91. Mounting plate 50 and front panel 14 of diaper 12 are captured by and between washer 95 captured by and between head 93 of fastener 90 and outer surface 21B of inner layer 21 of front panel 14 of diaper 12, and electrical connector 70 applied against outer face 52 of mounting plate 50.

Looking to FIGS. 4-7, alarm unit 31 consists of a chassis formed of plastic, ceramic, or other substantially rigid materials or combination of materials, and is preferably non-conductive. The chassis is formed by a planar base wall 100 having opposed inner and outer surfaces 101 and 102, a perimeter marginal extremity or edge 103, and a continuous sidewall 104. Continuous sidewall 104 is formed with perimeter edge 103, and projects outwardly and away from perimeter edge 103 terminating with continuous marginal extremity or edge 105. Sidewall 104 and inner surface 101 of base wall 100 cooperate to form a volume 106, and perimeter edge 105 bounds an opening 107 leading to volume 106.

Figure 4:
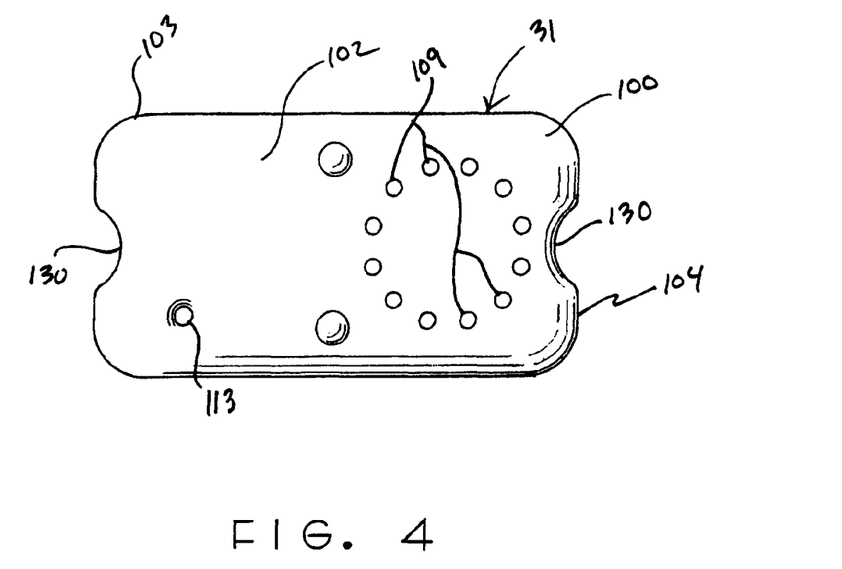
FIG. 4 is a rear elevation view of the alarm unit of FIG. 1.

The described chassis of alarm unit 31 supports the working components of alarm unit 31, which are applied to volume 106 and which are secured to inner surface 101 of base wall 100, such as with an adhesive. Looking to FIG. 5, the working components of alarm unit 31 are a conventionally-structured battery 110, a processor formed by a conventionally-structured circuit board 111, a conventionally-structured speaker 112, and a light 113 shown in FIG. 4, which is exposed at outer surface 102 of base wall 100. Battery 110 is electrically connected to supply power to circuit board 111. Circuit board 111 is electrically connected to speaker 112 with electrical wiring 120. Circuit board 111 is also electrically coupled to electrical connector 121 of alarm unit 31 with electrical wiring 122, and is electrically coupled to electrical connector 123 of alarm unit 31 with electrical wiring 124. As such, circuit board 111 is electrically connected to speaker 112 and electrical connectors 121 and 123, and speaker 112 is, therefore, electrically connected to electrical connectors 121 and 123 via circuit board 111 and the electrical wiring formed between circuit board 111 and speaker 112 and between circuit board 111 and electrical connectors 121 and 123. Speaker 112 is an alarm, which when activated issues an audible alarm stimulus, namely, and audible alarm or siren. A pattern of openings 109 shown in FIGS. 1 and 4 is formed through base wall 100 opposite to speaker 112 to convey the audible alarm or siren outwardly from volume 106 of the chassis within which speaker 112 is mounted. Light 113 is also an alarm, which when activated issues a visual alarm stimulus, namely, light or illumination produced through the activation and thus illumination of light 113. Light 113 is preferably a bright, full-spectrum light emitting diode (LED), and may, in other examples, be a limited spectrum LED configured to illuminate red, yellow, orange, blue, etc. The activation and illumination of light 113 can be in the form of a continuous illumination, a blinking illumination, etc.

Electrical connectors 121 and 123 of alarm unit 31 relate to electrical connectors 60 and 70, respectively, of conductor assembly 30. Electrical connectors 121 and 123 are complementing electrical connectors with respect to electrical connectors 60 and 70, respectively, of conductor assembly 30, and receive and detachably secure electrical connectors 60 and 70, respectively, of conductor assembly 30 as shown in FIG. 9. Electrical connectors 60 and 70 of conductor assembly 30 are conventionally structured male electrical connectors, and electrical connectors 121 and 123 of alarm unit 31 are corresponding conventionally structured female electrical connectors that receive and detachably secure electrical connectors 60 and 70 of conductor assembly 30, which not only detachably secures alarm unit 31 to conductor assembly 30 at mounting plate 50, but also electrically connects electrical connectors 121 and 123 of alarm unit 31 to electrical connectors 60 and 70, respectively, of conductor assembly 30. The detachable securement between electrical connectors 121 and 123 of alarm unit 31 and electrical connectors 60 and 70 of conductor assembly 30 is a detachable snap engagement, whereby electrical connectors 60 and 70 of conductor assembly 30 are snap received in and by electrical connectors 121 and 123 of alarm unit 31.

Figure 5:
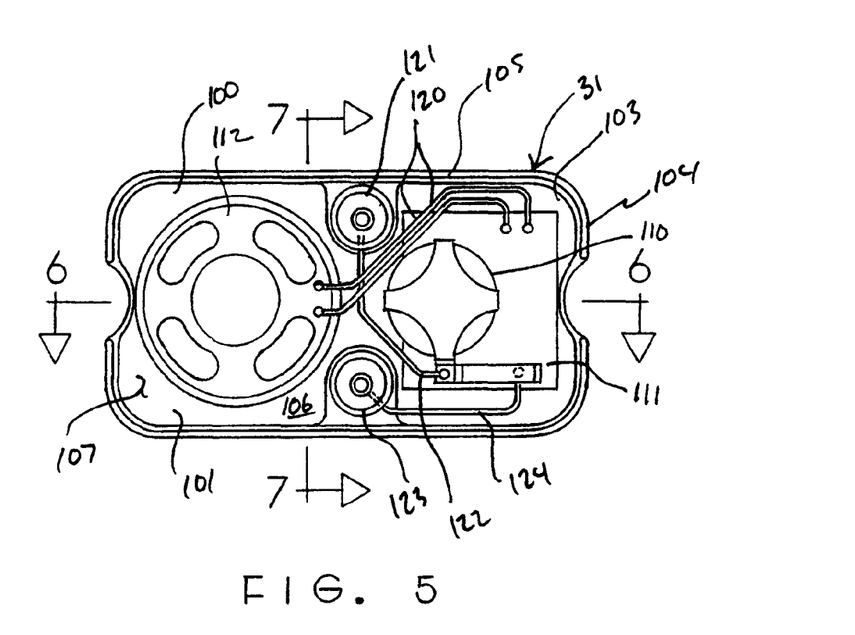
FIG. 5 is a front elevation view of the alarm unit of FIG. 4.
Figure 6:
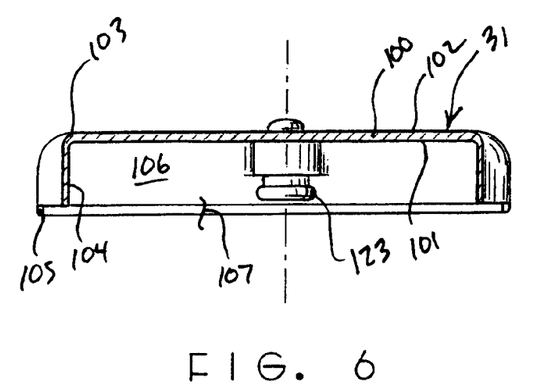
FIG. 6 is a section view taken along line 6-6 of FIG. 5.
Figure 7:
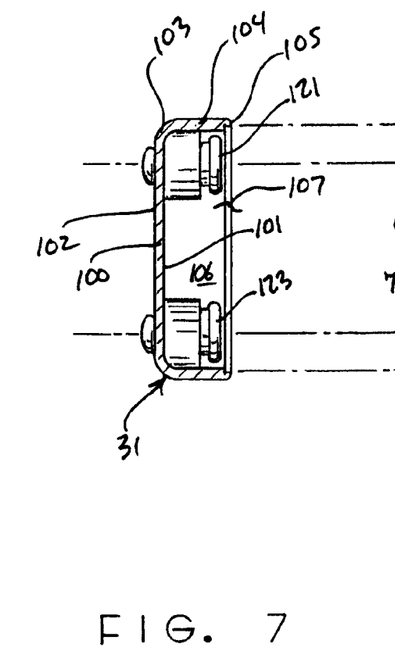
FIG. 7 is a section view taken along line 7-7 of FIG. 6.

To install alarm unit 31 to conductor assembly 30 to form system 11, alarm unit 31 is taken up, such as by hand, and is positioned opposite to outer face 52 of mounting plate 50 to align electrical connectors 121 and 123 of alarm unit 31 with electrical connectors 60 and 70, respectively, of conductor assembly 31. Alarm unit 31 is moved toward outer face 52 of mounting plate 50 applying and receiving electrical connectors 60 and 70 of conductor assembly 30 into electrical connectors 121 and 123, respectively, of alarm unit 31 as seen in FIG. 9 snappingly securing electrical connectors 60 and 70 of conductor assembly 30 to electrical connectors 121 and 123, respectively, of alarm unit 31, which detachably secures alarm unit 31 to, or otherwise with respect to, mounting plate 50 of conductor assembly 30 and electrically connects electrical connectors 60 and 70 of conductor assembly 30 to electrical connectors 121 and 123 of alarm unit 31. In this installed position of alarm unit 31 with respect to mounting plate 50 of conductor assembly 31, perimeter edge 105 of the chassis of alarm unit 31 is received in juxtaposition with outer face 52 of mounting plate 50 as substantially shown in FIG. 9, which closes opening 107 to volume 106 thus enclosing volume 106 of the chassis of alarm unit 31 enclosing the above-described working components of alarm unit 31 in volume 106 between the chassis of alarm unit 31 and outer face 52 of mounting plate 50, in accordance with the principle of the invention. Alarm unit 31 may be detached from conductor assembly 31 simply by grasping alarm unit 31 by hand and forcibly pulling alarm unit 31 away from outer face 52 of mounting plate 50 to detach electrical connectors 121 and 123 of alarm unit 31 from electrical connectors 60 and 70 of conductor assembly 30. To assist a user in taking up alarm unit 31, sidewall 104 is conveniently formed with opposed finger holds or indentions 130 as shown in FIGS. 1, 4, and 5.

The above-described installation of alarm unit 31 to conductor assembly 30 as described above and as illustrated in FIGS. 1 and 9 forms system 11 in diaper 12, and a conventionally structured circuit between alarm unit 31 and conductor assembly 30 produced by the electrical coupling between alarm unit 31 and conductor assembly 30 via the electrical engagement between electrical connectors 121 and 123 of alarm unit 31 and electrical connectors 60 and 70 of conductor assembly 30. The formed circuit is open when conductors 40 and 41 formed in diaper 12 are not electrically connected, and is closed when conductors 40 and 41 are electrically connected in response to interaction of conductors 40 and 41 with wetness applied to diaper 12 causing an electrical connection between conductors 40 and 41 in diaper 12. In response to a closing of this circuit formed between alarm unit 31 and conductor assembly 30 produced in response to wetness applied to the diaper electrically connecting conductors 40 and 41 applied to diaper 12, alarm unit 31 activates and issues alarm stimulus to alert a caregiver that wetness is applied to diaper 12 to indicated to the caregiver that diaper 12 needs to be changed. In particular, in response to a closing of this circuit formed between alarm unit 31 and conductor assembly 30 produced in response to wetness applied to the diaper electrically connecting conductors 40 and 41 applied to diaper 12, speaker 112 of alarm unit 31 activates to issue an audible alarm or siren to indicate that wetness is applied to diaper 12, and light 113 of alarm unit 31 activates to become illuminated forming a visual illumination stimulus to indicate that wetness is applied to diaper 12. The audible alarm issued by speaker 112 can be any audible alarm, such as a beep, a series of beeps, or other sound, a siren, a song, a preprogrammed message such as a verbal message such as "diaper is wet," "diaper needs to be changed," or the like. The illumination of light 113 can be a constant illumination, a flashing illumination, etc. To change diaper 12, alarm unit 31 is detached from conductor assembly 30 formed in diaper 12 severing the closed circuit deactivating speaker 112 and light 113 of alarm unit 31. Diaper 12 is removed and replaced with a fresh diaper incorporating a conductor assembly constructed and arranged in accordance with the principle of the invention, and alarm unit 31 is installed with the conductor assembly of the fresh diaper. The ability to operatively and detachably secure alarm unit 31 to a diaper formed with a conductor assembly constructed and arranged in accordance with the principle of the invention allows alarm unit 31 to be constantly reused with fresh diapers formed with conductor assemblies constructed and arranged in accordance with the principle of the invention.

In the present embodiment, electrical connector 60 of conductor assembly 30 is a conventionally structured male electrical connector and electrical connector 121 of alarm unit 31 is a corresponding conventionally structured female electrical connector, and this arrangement can be reversed if so desired. Furthermore, electrical connector 70 of conductor assembly 30 is a conventionally structured male electrical connector and electrical connector 123 of alarm unit 31 is a corresponding conventionally structured female electrical connector, and this arrangement can likewise be reversed if so desired.

The invention has been described above with reference to a preferred embodiment. However, those skilled in the art will recognize that changes and modifications may be made to the embodiment without departing from the nature and scope of the invention. Various changes and modifications to the embodiment herein chosen for purposes of illustration will readily occur to those skilled in the art. To the extent that such modifications and variations do not depart from the spirit of the invention, they are intended to be included within the scope thereof.

Having fully described the invention in such clear and concise terms as to enable those skilled in the art to understand and practice the same, the invention claimed is:

1. A diaper apparatus, comprising:
   a diaper including opposed inner and outer layers, each having an inner surface and an opposed outer surface, and absorbent material formed between the inner surfaces of the opposed inner and outer layers;

two conductors applied to the diaper to interact with wetness applied to the diaper;

a substantially rigid mounting plate, formed with two electrical connectors, affixed to the diaper, the mounting plate having an inner face applied against the outer surface of the outer layer of the diaper and an opposed outer face;

the two electrical connectors are electrically connected to the two conductors, respectively, and project outward with respect to the outer face of the mounting plate;

an alarm unit having two complementing electrical connectors, and an alarm electrically connected to the two complementing electrical connectors;

the two electrical connectors of the mounting plate detachably secure the two complementing electrical connectors, respectively, of the alarm unit to detachably secure the alarm unit to the mounting plate in juxtaposition to the outer face of the mounting plate, and electrically connect the two electrical connectors of the mounting plate to the two complementing electrical connectors of the alarm unit; and the alarm of the alarm unit issues an alarm stimulus in response to wetness applied to the diaper that electrically connects the two conductors applied to the diaper.

2. A diaper apparatus according to claim 1, wherein each electrical connector of the mounting plate is one of a male electrical connector and a female electrical connector, and each complementing electrical connector of the alarm unit is the other of the male electrical connector and the female electrical connector.

3. A diaper apparatus according to claim 1, wherein the two electrical connectors of the mounting plate snap engage and secure the two complementing electrical connectors of the alarm unit detachably securing the alarm unit to the mounting plate in juxtaposition to the outer face of the mounting plate.

4. A diaper apparatus, comprising:
a diaper including opposed inner and outer layers, each having an inner surface and an opposed outer surface, and absorbent material formed between the inner surfaces of the opposed inner and outer layers;

two conductors applied to the diaper capable of being electrically connected and indicating wetness applied to the diaper;

a substantially rigid mounting plate, affixed to the diaper with two fasteners, each formed with an electrical connector, the mounting plate having an inner face applied against the outer surface of the outer layer of the diaper and an opposed outer face;

the two electrical connectors of the two fasteners are electrically connected to the two conductors, are juxtaposed with respect to the outer face of the mounting plate, and project outward with respect to the outer face of the mounting plate;

an alarm unit having two complementing electrical connectors, and an alarm electrically connected to the two complementing electrical connectors; and the two electrical connectors of the fasteners secure the two complementing electrical connectors, respectively, of the alarm unit to detachably secure the alarm unit to the mounting plate in juxtaposition to the outer face of the mounting plate and electrically connect the two electrical connectors of the fasteners to the two complementing electrical connectors of the alarm unit.

5. A diaper apparatus according to claim 4, wherein each electrical connector is one of a male electrical connector and a female electrical connector, and each complementing electrical connector is the other of the male electrical connector and the female electrical connector.

6. A diaper apparatus according to claim 5, wherein the electrical connectors further comprise snap electrical connectors, and the complementing electrical connectors further comprise complementing snap electrical connectors to snappingly engage and secure the snap electrical connectors, respectively.

7. A diaper apparatus according to claim 4, wherein the fasteners comprise electrically conducting rivets that extend through the diaper from the inner layer to the outer layer and through the mounting plate to outer ends each secured to one of the electrical connectors juxtaposed along the outer face of the mounting plate.

8. A diaper apparatus, comprising:
a diaper including opposed inner and outer layers, each having an inner surface and an opposed outer surface, and absorbent material formed between the inner surfaces of the opposed inner and outer layers;

two conductors applied to the diaper to be electrically connected by wetness applied to the diaper;

a substantially rigid mounting plate affixed to the diaper with two fasteners each formed with an electrical connector, the mounting plate having an inner face applied against the outer surface of the outer layer of the diaper and an opposed outer face;

the two electrical connectors juxtaposed with respect to the outer face of the mounting plate and projecting outward with respect to the outer face of the mounting plate;

the two electrical connectors of the two fasteners electrically connect the two conductors, respectively;

an alarm unit having two complementing electrical connectors, and an alarm electrically connected to the two complementing electrical connectors;

the two electrical connectors of the fasteners detachably secure the two complementing electrical connectors, respectively, of the alarm unit to a) detachably secure the alarm unit to the mounting plate in juxtaposition to the outer face of the mounting plate, and b) electrically connect the two electrical connectors of the fasteners to the two complementing electrical connectors of the alarm unit; and the alarm of the alarm unit issues an alarm stimulus in response to wetness applied to the diaper that electrically connects the two conductors applied to the diaper.

9. A diaper apparatus according to claim 8, wherein each electrical connector is one of a male electrical connector and a female electrical connector, and each complementing electrical connector is the other of the male electrical connector and the female electrical connector.

10. A diaper apparatus according to claim 9, wherein the electrical connectors further comprise snap electrical connectors, and the complementing electrical connectors further comprise complementing snap electrical connectors snappingly engaging and securing the snap electrical connectors, respectively.

11. A diaper apparatus according to claim 10, wherein the fasteners comprise electrically conducting rivets that extend through the diaper from the inner layer to the outer layer and through the mounting plate to outer ends each secured to one of the electrical connectors juxtaposed along the outer face of the mounting plate.

* * * * *